United States Patent
Laine et al.

(10) Patent No.: US 7,598,267 B2
(45) Date of Patent: Oct. 6, 2009

(54) MUSCARINIC ACETYLCHOLINE RECEPTOR ANTAGONISTS

(75) Inventors: Dramane I. Laine, King of Prussia, PA (US); Brent W. McCleland, King of Prussia, PA (US); Christopher E. Neipp, King of Prussia, PA (US); Michael R. Palovich, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 202 days.

(21) Appl. No.: 11/568,930

(22) PCT Filed: May 10, 2005

(86) PCT No.: PCT/US2005/016148

§ 371 (c)(1),
(2), (4) Date: Nov. 10, 2006

(87) PCT Pub. No.: WO2005/112644

PCT Pub. Date: Dec. 1, 2005

(65) Prior Publication Data

US 2007/0173646 A1    Jul. 26, 2007

Related U.S. Application Data

(60) Provisional application No. 60/570,581, filed on May 13, 2004.

(51) Int. Cl.
*A01N 43/90* (2006.01)
*C07D 453/02* (2006.01)

(52) U.S. Cl. .................................. 514/305; 546/133

(58) Field of Classification Search .................. 546/133; 514/305
See application file for complete search history.

(56) References Cited

U.S. PATENT DOCUMENTS

| | | | |
|---|---|---|---|
| 2,800,478 A | 7/1957 | Zirkle et al. | |
| 2,800,481 A | 7/1957 | Zirkle et al. | |
| 3,634,852 A | 1/1972 | Hartley et al. | |
| 5,590,645 A | 1/1997 | Davies et al. | |
| 5,681,841 A | 10/1997 | Himmelsbach et al. | 514/326 |
| 5,780,466 A | 7/1998 | Emonds-Alt et al. | |
| 5,860,419 A | 1/1999 | Davies et al. | |
| 5,873,360 A | 2/1999 | Davies et al. | |
| 6,248,752 B1 | 6/2001 | Smith | |
| 6,262,066 B1 | 7/2001 | Tulshian et al. | |
| 6,350,758 B1 | 2/2002 | Kozikowski et al. | |
| 6,455,527 B2 | 9/2002 | Tulshian et al. | |
| 6,696,462 B2 | 2/2004 | Eickmeier et al. | |
| 6,750,226 B2 | 6/2004 | Forner et al. | |
| 7,232,841 B2 | 6/2007 | Busch-Petersen et al. | |
| 7,276,521 B2 | 10/2007 | Busch-Petersen et al. | |
| 7,439,255 B2 | 10/2008 | Wan et al. | |
| 2005/0020660 A1 | 1/2005 | Guyaux et al. | |
| 2005/0113417 A1 | 5/2005 | Mammen et al. | |
| 2005/0209272 A1 | 9/2005 | Fernandez et al. | |
| 2005/0277676 A1 | 12/2005 | Laine et al. | |
| 2006/0160844 A1 | 7/2006 | Belmonte et al. | |
| 2006/0178395 A1 | 8/2006 | Belmonte et al. | |
| 2006/0178396 A1 | 8/2006 | Belmonte et al. | |
| 2007/0135478 A1 | 6/2007 | Palovich et al. | |
| 2007/0149598 A1 | 6/2007 | Busch-Petersen et al. | |
| 2007/0179131 A1 | 8/2007 | Jin et al. | |
| 2007/0179180 A1 | 8/2007 | Busch-Petersen et al. | |
| 2007/0179184 A1 | 8/2007 | Busch-Petersen et al. | |
| 2007/0185088 A1 | 8/2007 | Busch-Petersen et al. | |
| 2007/0185090 A1 | 8/2007 | Busch-Petersen et al. | |
| 2007/0185148 A1 | 8/2007 | Busch-Petersen et al. | |
| 2007/0185155 A1 | 8/2007 | Laine et al. | |
| 2007/0232599 A1 | 10/2007 | Palovich et al. | |
| 2007/0238751 A1 | 10/2007 | Laine et al. | |
| 2007/0238752 A1 | 10/2007 | Busch-Petersen et al. | |
| 2007/0244150 A1 | 10/2007 | Busch-Petersen et al. | |
| 2007/0249664 A1 | 10/2007 | Laine et al. | |
| 2007/0270456 A1 | 11/2007 | Wan et al. | |
| 2007/0293531 A1 | 12/2007 | Busch-Petersen et al. | |
| 2008/0194618 A1 | 8/2008 | Laine et al. | |
| 2008/0234315 A1 | 9/2008 | Busch-Petersen et al. | |
| 2008/0249127 A1 | 10/2008 | Laine et al. | |
| 2008/0275079 A1 | 11/2008 | Busch-Petersen et al. | |
| 2008/0287487 A1 | 11/2008 | Cooper et al. | |

FOREIGN PATENT DOCUMENTS

| | | |
|---|---|---|
| EP | 0069715 | 6/1982 |
| EP | 0479481 | 4/1992 |
| FI | 56182 | 12/1976 |
| GB | 2064336 | 6/1981 |

(Continued)

OTHER PUBLICATIONS

Alabaster et al., Life sciences, (1997) vol. 60, No. 13-14, pp. 1053-1060.*

(Continued)

*Primary Examiner*—D. Margaret Seaman
*Assistant Examiner*—Niloofar Rahmani
(74) *Attorney, Agent, or Firm*—Dara L. Dinner; Charles M. Kinzig

(57) ABSTRACT

Muscarinic Acetylcholine Receptor Antagonists and methods of using them are provided.

42 Claims, No Drawings

FOREIGN PATENT DOCUMENTS

| | | |
|---|---|---|
| GB | 2129691 | 5/1984 |
| GB | 2169265 | 7/1986 |
| GB | 2178965 | 2/1987 |
| GB | 2242134 | 9/1991 |
| WO | 87/05213 | 9/1987 |
| WO | WO 97/10222 | 3/1997 |
| WO | 2005/087236 | 3/2005 |
| WO | 2006/050239 | 5/2006 |
| WO | 2006/055503 | 5/2006 |
| WO | 2006/055553 | 5/2006 |
| WO | 2006/062883 | 6/2006 |
| WO | 2006/062931 | 6/2006 |
| WO | 2006/065755 | 6/2006 |
| WO | 2006/065788 | 6/2006 |
| WO | 2006/017767 | 8/2006 |
| WO | 2007/018508 | 2/2007 |
| WO | 2007/018514 | 2/2007 |

OTHER PUBLICATIONS

Taft et al., Journal of the American Chemical Society (1974), 96(4), 1236-8.*
Brown, *History and Basic Properties*, Humana Press, USA pp. 7-9 (1989).
Caulfield, *Pharmac. Ther.*, vol. 58 pp. 319-379 (1993).
Costello, et al., *American Journal of Physiology*, vol. 276 (5) pp. L709-L714 (1999).
Fryer and Jacoby, *Am J Respir Crit Care Med*, vol. 158 (5, pt 3) pp. 154-160 (1998).
Fryer et al., *Life Sci*, vol. 64 (6-7) pp. 449-455 (1999).
Hedge, et al., *Life Sciences*, vol. 64 (6/7) pp. 419-428 (1999).
Ikeda, et al., *Naunyn-Schmiedeberg's Arch Pharmacol.*, vol. 366, pp. 97-103, (2002).
Minette, et al., *Journal of Applied Physiology*, vol. 67(6) pp. 2461-2465 (1989).
Oprins, et al., *Annals of the New York Academy of Sciences*, vol. 915 pp. 102-106 (2000).
Pauwels et al., *Am. J. Respir. Crit. Care Med.*, vol. 163 pp. 1256-1276 (2001).
Ran, et al., *Yaoxue Xuebao*, vol. 19 (5) pp. 361-366 (1984) Abstract only.
Sarau, *Mol. Pharmacol.*, vol. 56 (3) p. 657-63 (1999).
Van Rossum, et al., *Arch. Int. Pharmacodyn.*, vol. 143 p. 299 (1963).
Wu, et al., *Zhongguo Yaowu Huaxue Zazhi*, vol. 3 (1) pp. 23-26 (1993)Abstract only.
Zirkle, et al., *J Med Chem*, vol. 27 pp. 1269-1279 (1962).
Zirkle, et al., *J Med Chem*, vol. 27 pp. 1279-1285 (1962).
Zirkle, et al., *J Med Chem*, vol. 5 pp. 341-356 (1962).
Zhang, et al., *J Med Chem*, vol. 44 pp. 3937-3945 (2001).
Ran, et al., *Yaoxue Xuebao*, vol. 19 (5) pp. 361-366 (1984), with translation.
Wu, et al., *Zhongguo Yaowu Huaxue Zazhi*, vol. 3(1) pp. 23-26 (1993), with translation.
Yu, et al., *Yaoxue Xuebao*, vol. 18(10) pp. 766-774 (1983), with translation.
Zhang, et al., *Yaoxue Xuebao*, vol. 20(10) pp. 752-758 (1985), with translation.

* cited by examiner

MUSCARINIC ACETYLCHOLINE RECEPTOR ANTAGONISTS

This application is a 371 of International Application No. PCT/US2005/016148, filed 10 May 2005, which claims priority of U.S. Provisional Application No. 60/570,581, filed 13 May 2004.

FIELD OF THE INVENTION

This invention relates to novel quinuclidines derivatives, pharmaceutical compositions, and use thereof in treating muscarinic acetylcholine receptor mediated diseases of the respiratory tract.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors that have seven transmembrane domains. There are five subtypes of mAChRs, termed $M_1$-$M_5$, and each is the product of a distinct gene. Each of these five subtypes displays unique pharmacological properties. Muscarinic acetylcholine receptors are widely distributed in vertebrate organs where they mediate many of the vital functions. Muscarinic receptors can mediate both inhibitory and excitatory actions. For example, in smooth muscle found in the airways, $M_3$ mAChRs mediate contractile responses. For review, please see Caulfield (1993 *Pharmac. Ther.* 58:319-79).

In the lungs, mAChRs have been localized to smooth muscle in the trachea and bronchi, the submucosal glands, and the parasympathetic ganglia. Muscarinic receptor density is greatest in parasympathetic ganglia and then decreases in density from the submucosal glands to tracheal and then bronchial smooth muscle. Muscarinic receptors are nearly absent from the alveoli. For review of mAChR expression and function in the lungs, please see Fryer and Jacoby (1998 *Am J Respir Crit Care Med* 158(5, pt 3) S 154-60).

Three subtypes of mAChRs have been identified as important in the lungs, $M_1$, $M_2$ and $M_3$ mAChRs. The $M_3$ mAChRs, located on airway smooth muscle, mediate muscle contraction. Stimulation of $M_3$ mAChRs activates the enzyme phospholipase C via binding of the stimulatory G protein Gq/11 (Gs), leading to liberation of phosphatidyl inositol-4,5-bisphosphate, resulting in phosphorylation of contractile proteins. $M_3$ mAChRs are also found on pulmonary submucosal glands. Stimulation of this population of $M_3$ mAChRs results in mucus secretion.

$M_2$ mAChRs make up approximately 50-80% of the cholinergic receptor population on airway smooth muscles. Although the precise function is still unknown, they inhibit catecholaminergic relaxation of airway smooth muscle via inhibition of cAMP generation. Neuronal $M_2$ mAChRs are located on postganglionic parasympathetic nerves. Under normal physiologic conditions, neuronal $M_2$ mAChRs provide tight control of acetylcholine release from parasympathetic nerves. Inhibitory $M_2$ mAChRs have also been demonstrated on sympathetic nerves in the lungs of some species. These receptors inhibit release of noradrenaline, thus decreasing sympathetic input to the lungs.

$M_1$ mAChRs are found in the pulmonary parasympathetic ganglia where they function to enhance neurotransmission. These receptors have also been localized to the peripheral lung parenchyma, however their function in the parenchyma is unknown.

Muscarinic acetylcholine receptor dysfunction in the lungs has been noted in a variety of different pathophysiological states. In particular, in asthma and chronic obstructive pulmonary disease (COPD), inflammatory conditions lead to loss of inhibitory $M_2$ muscarinic acetylcholine autoreceptor function on parasympathetic nerves supplying the pulmonary smooth muscle, causing increased acetylcholine release following vagal nerve stimulation (Fryer et al. 1999 *Life Sci* 64 (6-7) 449-55). This mAChR dysfunction results in airway hyperreactivity and hyperresponsiveness mediated by increased stimulation of $M_3$ mAChRs. Thus the identification of potent mAChR antagonists would be useful as therapeutics in these mAChR-mediated disease states.

COPD is an imprecise term that encompasses a variety of progressive health problems including chronic bronchitis, chronic bronchiolitis and emphysema, and it is a major cause of mortality and morbidity in the world. Smoking is the major risk factor for the development of COPD; nearly 50 million people in the U.S. alone smoke cigarettes, and an estimated 3,000 people take up the habit daily. As a result, COPD is expected to rank among the top five as a world-wide health burden by the year 2020. Inhaled anti-cholinergic therapy is currently considered the "gold standard" as first line therapy for COPD (Pauwels et al. 2001 *Am. J Respir. Crit. Care Med.* 163:1256-1276).

Despite the large body of evidence supporting the use of anti-cholinergic therapy for the treatment of airway hyperreactive diseases, relatively few anti-cholinergic compounds are available for use in the clinic for pulmonary indications. More specifically, in United States, Ipratropium Bromide (Atrovent©; and Combivent©, in combination with albuterol) is currently the only inhaled anti-cholinergic marketed for the treatment of airway hyperreactive diseases. While this compound is a potent anti-muscarinic agent, it is short acting, and thus must be administered as many as four times daily in order to provide relief for the COPD patient. In Europe and Asia, the long-acting anti-cholinergic Tiotropium Bromide (Spiriva©) was recently approved, however this product is currently not available in the United States. Thus, there remains a need for novel compounds that are capable of causing blockade at mAChRs which are long acting and can be administered once-daily for the treatment of airway hyperreactive diseases such as asthma and COPD.

Since mAChRs are widely distributed throughout the body, the ability to apply anti-cholinergics locally and/or topically to the respiratory tract is particularly advantageous, as it would allow for lower doses of the drug to be utilized. Furthermore, the ability to design topically active drugs that have long duration of action, and in particular, are retained either at the receptor or by the lung, would allow the avoidance of unwanted side effects that may be seen with systemic anti-cholinergic use.

SUMMARY OF THE INVENTION

This invention provides for a method of treating a muscarinic acetylcholine receptor (mAChR) mediated disease, wherein acetylcholine binds to an mAChR and which method comprises administering an effective amount of a compound of Formula (I) or a pharmaceutically acceptable salt thereof.

This invention also relates to a method of inhibiting the binding of acetylcholine to its receptors in a mammal in need thereof which comprises administering to aforementioned mammal an effective amount of a compound of Formula (I).

The present invention also provides for the novel compounds of Formula (I), and pharmaceutical compositions comprising a compound of Formula (I), and a pharmaceutical carrier or diluent.

Compounds of formula (I) useful in the present invention are represented by the structure:

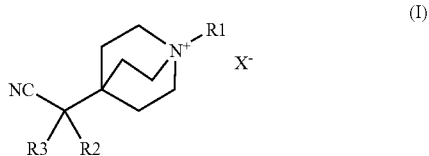

wherein:

R1 is selected from the group consisting of C1-15 alkyl, halosubstituted C1-15 alkyl, C1-15 alkyl cycloalkyl, cycloalkyl, C2-15 alkenyl, hydroxy substituted C1-15 alkyl, C1-15 alkyl aryl, C1-15 alkyl heteroaryl, (CR7R7)qNRaRa, (CR7R7)qNC(O)Ra, (CR7R7)qC(O)NRaRa, (CR7R7)qC(O)Ra, (CR7R7)qOC(O)Ra, (CR7R7)qNRaC(O)NRaRa, (CR7R7)qORc and (CR7R7)qNS(0)₂Ra; or R1 is selected from the group consisting of:

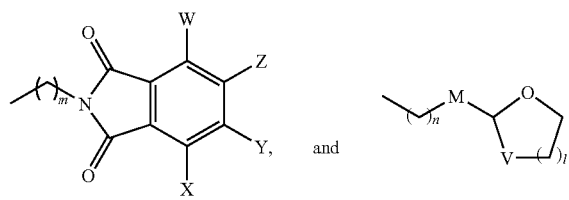

R1 is selected from the group consisting of:

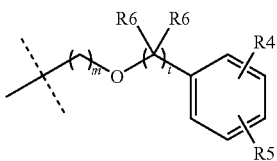

R2 and R3 are, independently, selected from the group consisting of aryl, C1-4 alkyl aryl, heteroaryl, C1-4 alkyl heteroaryl, heterocyclic and a heterocyclic C1-4 alkyl heterocyclic moiety all of which moieties may be optionally substituted;

Ra is selected from the group consisting of hydrogen, C1-15 alkyl, C1-15 alkoxy, aryl, C1-15 alkyl aryl, heteroaryl, C1-15 alkyl heteroaryl and a C1-15 alkyl heterocyclic moiety, all of which moieties may be optionally substituted;

Rc is selected from the group consisting of hydrogen, C1-15 alkyl, C1-15 alkoxy, heterocyclic and a C1-15 alkyl heterocyclic moiety, all of which moieties may be optionally substituted;

R4 and R5 are independently selected from the group consisting of hydrogen, halogen, C1-4 alkyl, aryl, C1-4 alkyl aryl, cyano, nitro, (CR7R7)pORb, (CR7R7)pNRbRb, or R4 and R5 together may form a 5 to 6 membered saturated or unsaturated ring; and wherein the alkyl, aryl, arylalkyl, heteroaryl, heteroalkyl, heterocyclic, heterocyclicalkyl groups may be optionally substituted;

R6 is selected from the group consisting of hydrogen, C1-4 alkyl;

q is 0 or an integer having a value of 1 to 15;
n is an integer having a value of 1 to 14;
m is an integer having a value of 1 to 15;
l is an integer having a value of 1 to 4;
t is 0 or an integer having a value of 1 to 5;
p is an integer having a value of 1 to 4;
X, Y, Z and W are, independently, selected from the group consisting of hydrogen, C1-4 alkyl;
M is 0 or CH₂;
V is selected from the group consisting of O, S, and NRb;
Rb is selected from the group consisting of hydrogen, C1-4 alkyl, aryl and C1-4 alkyl aryl;
R7 is selected from the group consisting of hydrogen, C1-4 alkyl, halosubstituted C1-4 alkyl, and hydroxy substituted C1-4 alkyl;
X— is a physiologically acceptable anion, such as chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

DETAILED DESCRIPTION OF THE INVENTION

This invention related to novel bi-aryl 8-azoniabicyclo [3.2.1]octane compounds, pharmaceutical compositions, processes for their preparation, and use thereof in treating mAChR mediated diseases.

In a preferred embodiment of the present invention the compound is of formula (I) herein below:

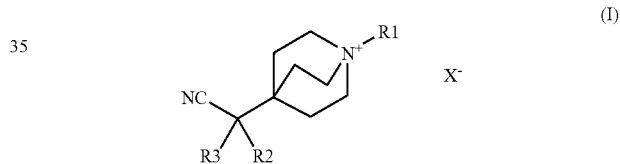

wherein:

R1 is selected from the group consisting of C1-10 alkyl, C1-10 alkyl aryl, C2-5 alkenyl, and (CR7R7)qORa,;
R2 and R3 are, independently, selected from the group consisting of phenyl and thiophene.
Ra is selected from the group consisting of hydrogen, C1-5 alkyl, C1-5 alkoxy, phenyl and benzyl, all of which moieties may be optionally substituted
q is 0 or an integer having a value of 1 to 5;
R7 is hydrogen, or C1-4 alkyl; and
X— is a physiologically acceptable anion, such as chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

All of the aryl, heteroaryl, and heterocyclic containing moieties may be optionally substituted as defined herein below.

For use herein the term "the aryl, heteroaryl, and heterocyclic containing moieties" refers to both the ring and the alkyl, or if included, the alkenyl rings, such as aryl, arylalkyl, and aryl alkenyl rings. The term "moieties" and "rings" may be interchangeably used throughout.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; $S(O)_{m'}$ $C_{1-10}$ alkyl, wherein m' is 0, 1 or 2, such as methyl thio, methyl sulfinyl or methyl sulfonyl; amino, mono & di-substituted amino, such as in the $NR_{10}R_{11}$ group; $NHC(O)R_9$; $C(O)$ $NR_{10}R_{11}$; $C(O)OH$; $S(O)_2NR_{10}R_{11}$; $NHS(O)_2R_9$, $C_{1-10}$ alkyl, such as methyl, ethyl, propyl, isopropyl, or t-butyl; halosubstituted $C_{1-10}$ alkyl, such $CF_3$; an optionally substituted aryl, such as phenyl, or an optionally substituted arylalkyl, such as benzyl or phenethyl, optionally substituted heterocyclic, optionally substituted heterocyclicalkyl, optionally substituted heteroaryl, optionally substituted heteroaryl alkyl, wherein these aryl, heteroaryl, or heterocyclic moieties may be substituted one to two times by halogen; hydroxy; hydroxy substituted alkyl; $C_{1-10}$ alkoxy; $S(O)_{m'}C_{1-10}$ alkyl; amino, mono & di-substituted alkyl amino, such as in the $NR_{10}R_{11}$ group; $C_{1-10}$ alkyl, or halosubstituted $C_{1-10}$ alkyl, such as $CF_3$.

The following terms, as used herein, refer to:
"halo"—all halogens, that is chloro, fluoro, bromo and iodo.
"$C_{1-10}$alkyl" or "alkyl"—both straight and branched chain moieties of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.
"cycloalkyl" is used herein to mean cyclic moiety, preferably of 3 to 8 carbons, including but not limited to cyclopropyl, cyclopentyl, cyclohexyl, and the like.
"alkenyl" is used herein at all occurrences to mean straight or branched chain moiety of 2-10 carbon atoms, unless the chain length is limited thereto, including, but not limited to ethenyl, 1-propenyl, 2-propenyl, 2-methyl-1-propenyl, 1-butenyl, 2-butenyl and the like.
"aryl"—phenyl and naphthyl;
"heteroaryl" (on its own or in any combination, such as "heteroaryloxy", or "heteroaryl alkyl")—a 5-10 membered aromatic ring system in which one or more rings contain one or more heteroatoms selected from the group consisting of N, O or S, such as, but not limited to, pyrrole, pyrazole, furan, thiophene, quinoline, isoquinoline, quinazolinyl, pyridine, pyrimidine, oxazole, tetrazole, thiazole, thiadiazole, triazole, imidazole, or benzimidazole.
"heterocyclic" (on its own or in any combination, such as "heterocyclicalkyl")—a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydropyran, thiomorpholine, or imidazolidine. Furthermore, sulfur may be optionally oxidized to the sulfone or the sulfoxide.
"arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.
"sulfinyl"—the oxide S (O) of the corresponding sulfide, the term "thio" refers to the sulfide, and the term "sulfonyl" refers to the fully oxidized $S(O)_2$ moiety.
"wherein two $R_1$ moieties (or two Y moieties) may together form a 5 or 6 membered saturated or unsaturated ring" is used herein to mean the formation of an aromatic ring system, such as naphthalene, or is a phenyl moiety having attached a 6 membered partially saturated or unsaturated ring such as a $C_6$ cycloalkenyl, i.e. hexene, or a $C_5$ cycloalkenyl moiety, such as cyclopentene.

Illustrative Compounds of Formula (I) Include:

4-[cyano(di-2-thienyl)methyl]-1-[3-(phenyloxy)propyl]-1-azoniabicyclo[2.2.2]octane bromide;

4-[cyano(diphenyl)methyl]-1-[3-(phenyloxy)propyl]-1-azoniabicyclo[2.2.2]octane bromide;

4-[cyano(diphenyl)methyl]-1-[2-(phenyloxy)ethyl]-1-azoniabicyclo[2.2.2]octane bromide;

4-[cyano(diphenyl)methyl]-1-[4-(phenyloxy)butyl]-1-azoniabicyclo[2.2.2]octane bromide;

4-[cyano(diphenyl)methyl]-1-{3-[(phenylmethyl)oxy]propyl}-1-azoniabicyclo[2.2.2]octane bromide;

4-[cyano(diphenyl)methyl]-1-nonyl-1-azoniabicyclo[2.2.2]octane bromide;

4-[cyano(diphenyl)methyl]-1-(2-phenylethyl)-1-azoniabicyclo[2.2.2]octane bromide;

4-[cyano(diphenyl)methyl]-1-[2-(methyloxy)ethyl]-1-azoniabicyclo[2.2.2]octane bromide;

4-[cyano(diphenyl)methyl]-1-ethyl-1-azoniabicyclo[2.2.2]octane bromide;

4-[cyano(diphenyl)methyl]-1-(2-{[2-(methyloxy)ethyl]oxy}ethyl)-1-azoniabicyclo[2.2.2]octane bromide;

4-[cyano(diphenyl)methyl]-1-(4-penten-1-yl)-1-azoniabicyclo[2.2.2]octane bromide;

1-azabicyclo[2.2.2]oct-4-yl(diphenyl)acetonitrile;

4-[cyano(diphenyl)methyl]-1-(3-hydroxypropyl)-1-azoniabicyclo[2.2.2]octane bromide;

Methods of Preparation

The compounds of Formula (I) may be obtained by applying synthetic procedures, some of which are illustrated in the Scheme below. The synthesis provided in this Scheme is applicable for producing compounds of Formula (I) having a variety of different R1, R2 and R3 groups which are reacted, employing substituents which are suitably protected, to achieve compatibility with the reactions outlined herein. Subsequent deprotection, in those cases, then affords compounds of the nature generally disclosed. While the Schemes are shown with compounds only of Formula (I), this is merely for illustration purpose only.

As shown in Scheme 1, the desired compounds of Formula (I) can be prepared in four synthetic steps from the commercially available ethyl 4-piperidinecarboxylate precursor 1. Compound 1 is reacted with 1-bromo-2-chloroethane following standard alkylation procedures well known in the art such as potassium carbonate in acetone followed by reaction of the intermediate with lithium diisopropylamide in an aprotic solvent such as tetrahydrofuran to give the quinuclidine intermediate 2. Condensation of compound 2 with organometallic reagents such as a Grignard reagent or an organolithium derivative in an aprotic solvent such as tetrahydrofuran, results in the formation of the tertiary alcohol 3 of Formula (I) (R1=nothing). Reaction of compound 3 with TMSCN and $AlCl_3$ in an aprotic solvent such as dichloroethane, results in the formation of the nitrile derivative 4 of Formula (I) (R1=nothing). Further N-alkylation of compound 4 with a suitable alkyl halide in a organic solvent such as chloroform or acetonitrile gives compound 5 of Formula (I) (R1 not nothing).

Scheme 1

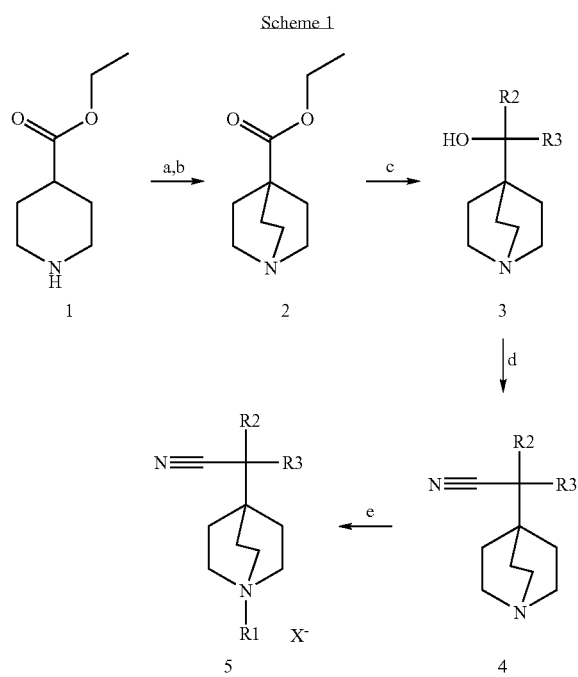

Reagents and conditions: a) 1-bromo-2-chloroethane, K₂CO₃, acetone; b) LDA, THF; c) R₂M then R₃M, THF; d) AlCl₃, TMSCN, DCE, 85° C.; e) R1X, ACN, CHCl₃.

SYNTHETIC EXAMPLES

The invention will now be described by reference to the following Examples, which are merely illustrative and are not to be construed as a limitation of the scope of the present invention. All temperatures are given in ° C. Thin layer chromatography (t.l.c.) was carried out on silica, and column chromatography on silica (Flash column chromatography using Merck 9385 unless stated otherwise).

The following are the experimental conditions for the LC-MS.

LC-MS Experimental Conditions:
Liquid Chromatograph:

| System: | Shimadzu LC system with SCL-10A Controller and dual UV detector |
|---|---|
| Autosampler: | Leap CTC with a Valco six port injector |
| Column: | Aquasil/Aquasil (C18 40 × 1 mm) |
| Inj. Volume (μL): | 2.0 |
| Solvent A: | H2O, 0.02% TFA |
| Solvent B: | MeCN, 0.018% TFA |
| Gradient: | linear |
| Channel A: | UV 214 nm |
| Channel B: | ELS |

| Step | Time (min) | Dura. (min) | Flow (μL/min) | Sol. A | Sol. B |
|---|---|---|---|---|---|
| 0 | 0.00 | 0.00 | 300.00 | 95.00 | 5.00 |
| 1 | 0.00 | 0.01 | 300.00 | 95.00 | 5.00 |
| 2 | 0.01 | 3.20 | 300.00 | 10.00 | 90.00 |
| 3 | 3.21 | 1.00 | 300.00 | 10.00 | 90.00 |
| 4 | 4.21 | 0.10 | 300.00 | 95.00 | 5.00 |
| 5 | 4.31 | 0.40 | 300.00 | 95.00 | 5.00 |

| Mass Spectrometer: | PE Sciex Single Quadrupole LC/MS API-150 |
|---|---|
| Polarity: | Positive |
| Acquisition mode: | Profile |

The Gilson preparatory HPLC was conducted under the following conditions:
Column: 75×33 mm I. D., S-5 um, 12 nm
Flow rate: 30 mL/min
Injection Volume: 0.800 mL
Room temperature
Solvent A: water
Solvent B: acetonitrile All solvents used herein are of the highest available purity and all reactions are run under anhydrous conditions under an air atmosphere unless otherwise indicated.

Example 1

Preparation of 1-azabicyclo[2.2.2]oct-4-yl(diphenyl)acetonitrile

Ethyl 1-(2-chloroethyl)-4-piperidinecarboxylate

To a solution of ethyl nipecotate (20.0 mL, 130 mmol) in acetone (180 mL) was added 1-bromo-2-chloroethane (21.6 mL, 260 mmol) followed by anhydrous K₂CO₃ (27.12 g, 196 mmol). The reaction mixture was stirred for 24 h and then concentrated under vacuum. The resulting residue was treated with H₂O (75 mL) and extracted with Et₂O. The combined organic layers were dried over MgSO₄, filtered, and concentrated under vacuum. Purification of the crude residue by flash chromatography (50% Et₂O/50% hexane) on silica gel gave the title compound (10.99 g, 38.6%). EI-MS m/z 220(M+H⁺) Rt (1.20 min).

Ethyl 1-azabicyclo[2.2.2]octane-4-carboxylate

A solution of ethyl 1-(2-chloroethyl)-4-piperidinecarboxylate (20.42 g, 92.9 mmol) in THF (600 mL) was cooled to −50° C. under Ar. LDA (2.0 M in heptane/THF/ethyl benzene, 70 mL, 140 mmol) was slowly added to the solution at −50° C. over 25 min. The reaction was allowed to warm up to room temperature overnight. The reaction was quenched with K₂CO₃ (saturated aqueous) (500 mL) and extracted with Et₂O (3×500 mL). The combined organic layers were dried over MgSO₄, filtered, and concentrated under vacuum. The resulting orange oil was co-evaporated three times with CH₂Cl₂ to remove excess ethyl benzene, resulting in the title compound (16.29 g, 95.7%). EI-MS m/z 184 (M+H⁺) Rt (1.08 min).

1-Azabicyclo[2.2.2]oct-4-yl(diphenyl)methanol

A solution of phenyllithium (1.5-1.7 M in 70 cyclohexane/30 ether, 20.0 mL, 32 mmol) was chilled down to −30° C. under Ar. Ethyl 1-azabicyclo[2.2.2]octane-4-carboxylate (1.51 g, 8.23 mmol) in THF (20 mL) was slowly added to the reaction mixture at −30° C. over 25 min. The reaction was allowed to warm up to room temperature overnight. The reaction was quenched with H₂O and then evaporated to dryness under vacuum. H₂O and EtOAc were added, causing a white solid to crash out. This solid was filtered off, to give the title compound (0.79 g). The aqueous phase was further extracted with EtOAc, the combined organic layers were dried over MgSO$_4$, filtered, and concentrated under vacuum. The crude product was treated with EtOAc and hexane and filtered to yield more of the title compound (0.67 g). Total yield (1.46 g, 60.7%). EI-MS m/z 294 (M+H$^+$) Rt (1.37 min).

General Procedure for the Conversion of a Tertiary Alcohol to a Nitrile Derivative 1-Azabicyclo[2.2.2]oct-4-yl(diphenyl)acetonitrile To a suspension of 1-azabicyclo[2.2.2]oct-4-yl(diphenyl) methanol (0.3055 g, 1.04 mmol) in 1,2-dichloroethane (17 mL) was added AlCl$_3$ (0.6675 g, 5.04 mmol). The reaction was allowed to stir for 10 min and then TMSCN (0.68 mL, 5.10 mmol) was added. The reaction was sealed and heated to 85° C. for overnight. The reaction mixture was poured into a separatory funnel containing K$_2$CO$_3$ (aq. sat.) (100 mL) and EtOAc (100 mL). The aqueous phase was separated and further extracted with EtOAc (3×100 mL) was performed. The combined organics were dried over MgSO$_4$, filtered and concentrated under vacuum. The residue was dissolved in DMSO and purified by Gilson preparatory HPLC (w/0.1% TFA). The combined fractions were concentrated down under vacuum to remove CH$_3$CN. The resulting water layer was basified to pH=12 with 6N NaOH, and then extracted with EtOAc. The combined organic fractions were dried over MgSO$_4$, filtered, and concentrated under vacuum to give the title compound (0.185 g, 59.7%). EI-MS ml/z 303 (M+H$^+$) Rt (1.76 min).

Example 2

Preparation of 4-[cyano(diphenyl)methyl]-1-[3-(phenyloxy)propyl]-1-azoniabicyclo[2.2.2]octane bromide General Procedure for Salt Formation Without HPLC Purification To a solution of 1-azabicyclo[2.2.2]oct-4-yl(diphenyl)acetonitrile (0.1468 g, 0.485 mmol) in 2CH$_3$CN/3CHCl$_3$ (10 mL) was added 3-bromopropyl phenyl ether (0.10 mL, 0.634 mmol). The solution was heated to 60° C. for 16 hours. The reaction was cooled to room temperature and concentrated under vacuum. The residue was taken up in ethyl acetate and hexane causing a solid to crash out of solution. This solid was filtered off, and washed with hexane to give the title compound (0.1986 g, 79.4%). EI-MS m/z 437(M$^+$) Rt (2.17 min).

Example 3

Preparation of 4-[cyano(diphenyl)methyl]-1-[2-(phenyloxy)ethyl]-1-azoniabicyclo[2.2.2]octane bromide Following the general procedure outlined in Example 2, 1-azabicyclo[2.2.2]oct-4-yl(diphenyl)acetonitrile (0.0499 g, 0.165 mmol) and 2-bromoethyl phenyl ether (0.0760 g, 0.378 mmol) in 2CH$_3$CN/3CHCl$_3$ (4.0 mL) were reacted to give the desired product (0.0548 g, 66.0%). EI-MS m/z 423(M$^+$) Rt (2.20 min).

Example 4

Preparation of 4-[cyano(diphenyl)methyl]-1-(2-phenylethyl)-1-azoniabicyclo[2.2.2]octane bromide Following the general procedure outlined in Example 2, 1-azabicyclo[2.2.2]oct-4-yl(diphenyl)acetonitrile (0.0470 g, 0.155 mmol) and (2-bromoethyl)benzene (0.045 mL, 0.329 mmol) in 2CH$_3$CN/3CHCl$_3$ (4.0 mL) were reacted to give the desired product (0.0457 g, 60.9%). EI-MS m/z 407(M$^+$) Rt (2.14 min).

Example 5

Preparation of 4-[cyano(diphenyl)methyl]-1-nonyl-1-azoniabicyclo[2.2.2]octane bromide Following the general procedure outlined in Example 2, 1-azabicyclo[2.2.2]oct-4-yl(diphenyl)acetonitrile (0.0495 g, 0.164 mmol) and 1-bromononane (0.050 mL, 0.262 mmol) in 2CH$_3$CN/3CHCl$_3$ (4.0 mL) were reacted to give the desired product (0.0652 g, 78.6%). EI-MS m/z 429 (M$^+$) Rt (2.55 min).

Example 6

Preparation of 4-[cyano(diphenyl)methyl]-1-(4-penten-1-yl)-1-azoniabicyclo[2.2.2]octane bromide Following the general procedure outlined in Example 2, 1-azabicyclo[2.2.2]oct-4-yl(diphenyl)acetonitrile (0.0495 g, 0.164 mmol) and 5-bromo-1-pentene (0.035 mL, 0.295 mmol) in 2CH$_3$CN/3CHCl$_3$ (4.0 mL) were reacted to give the desired product (0.0433 g, 59.3%). EI-MS m/z 371(M$^+$) Rt (2.03 min).

Example 7

Preparation of 4-[cyano(diphenyl)methyl]-1-[4-(phenyloxy)butyl]-1-azoniabicyclo[2.2.2]octane bromide General Procedure for Salt Formation with HPLC Purification To a solution of 1-azabicyclo[2.2.2]oct-4-yl(diphenyl)acetonitrile (0.0446 g, 0.147 mmol) in 2CH$_3$CN/3CHCl$_3$ (4.0 mL) was added 4-bromobutyl phenyl ether (0.0789 g, 0.344 mmol). The solution was heated to 60° C. for overnight. The reaction was cooled to room temperature and concentrated under vacuum. The residue was taken up in 2.5 mL of DMSO and purified by Gilson preparatory HPLC (without TFA) to give the title compound (0.0419 g, 53.7%). EI-MS m/z 451 (M$^+$) Rt (2.31 min).

Example 8

Preparation of 4-[cyano(diphenyl)methyl]-1-[2-(methyloxy)ethyl]-1-azoniabicyclo[2.2.2]octane bromide Following the general procedure outlined in Example 7, 1-azabicyclo[2.2.2]oct-4-yl(diphenyl)acetonitrile (0.0497 g, 0.164 mmol) and 2-bromoethyl methyl ether (0.030 mL, 0.319 mmol) in 2CH$_3$CN/3CHCl$_3$ (4.0 mL) were reacted to give the desired product (0.0169 g, 23.3%). EI-MS m/z 361 (M$^+$) Rt (1.84 min).

Example 9

Preparation of 4-[cyano(diphenyl)methyl]-1-{3-[(phenylmethyl)oxy]propyl}-1-azoniabicyclo[2.2.2]octane bromide Following the general procedure outlined in Example 7, 1-azabicyclo[2.2.2]oct-4-yl(diphenyl)acetonitrile (0.0495 g, 0.164 mmol) and 3-bromopropyl phenylmethyl ether (0.050 mL, 0.283 mmol) in 2CH$_3$CN/3CHCl$_3$ (4.0 mL) were reacted to give the desired product (0.0579 g, 66.6%). EI-MS m/z 451(M$^+$) Rt (2.28 min).

Example 10

Preparation of 4-[cyano(diphenyl)methyl]-1-(2-{[2-(methyloxy)ethyl]oxy}ethyl)-1-azoniabicyclo[2.2.2]octane bromide Following the general procedure outlined in Example 7, 1-azabicyclo[2.2.2]oct-4-yl(diphenyl)acetonitrile (0.0495 g, 0.164 mmol) and 1-bromo-2-{[2-(methyloxy)ethyl]oxy}ethane (0.040 mL, 0.265 mmol) in 2CH$_3$CN/3CHCl$_3$ (4.0 mL) were reacted to give the desired product (0.0431 g, 54.6%). EI-MS m/z 405 (M$^+$) Rt (1.85 min).

Example 11

Preparation of 4-[cyano(diphenyl)methyl]-1-(3-hydroxypropyl)-1-azoniabicyclo[2.2.2]octane bromide Following the general procedure outlined in Example 7, 1-azabicyclo[2.2.2]oct-4-yl(diphenyl)acetonitrile (0.0495 g, 0.164 mmol) and 3-bromo-1-propanol (0.030 mL, 0.343 mmol) in 2CH$_3$CN/3CHCl$_3$ (4.0 mL) were reacted to give the desired product (0.0467 g, 64.9%). EI-MS m/z 361 (M$^+$) Rt (1.98 min).

Example 12

Preparation of 4-[cyano(diphenyl)methyl]-1-ethyl-1-azoniabicyclo[2.2.2]octane bromide Following the general procedure outlined in Example 7, 1-azabicyclo[2.2.2]oct-4-yl(diphenyl)acetonitrile (0.0495 g, 0.164 mmol) and bromoethane (0.025 mL, 0.335 mmol) in 2CH$_3$CN/3CHCl$_3$ (4.0 mL) were reacted to give the desired product (0.0456 g, 68.1%). EI-MS m/z 331 (M$^+$) Rt (1.80 min).

Example 13

Preparation of 4-[cyano(di-2-thienyl)methyl]-1-[3-(phenyloxy)propyl]-1-azoniabicyclo[2.2.2]octane bromide 1-Azabicyclo[2.2.2]oct-4-yl(di-2-thienyl)methanol A solution of 2-thienyllithium (1.0 M in THF, 13.0 mL, 13 mmol) was chilled down to −30° C. under Ar. Ethyl 1-azabicyclo[2.2.2]octane-4-carboxylate (0.77 g, 4.20 mmol) in THF (12 mL) was slowly added to the 2-thienyllithium at −30° C. over 40 min. The reaction was allowed to warm up to room temperature for overnight. The reaction was quenched with H$_2$O and then diluted with EtOAC, hexane and DCM causing a solid to crash out of solution. The solid was filtered off, resulting in the desired compound (0.9132 g, 71.3%). EI-MS m/z 306(M$^+$) Rt (1.33 min).

1-Azabicyclo[2.2.2]oct-4-yl(di-2-thienyl)acetonitrile

Following the general procedure for cyano formation outlined in Example 1, 1-azabicyclo[2.2.2]oct-4-yl(di-2-thienyl)methanol (0.3065 g, 1.003 mmol), AlCl$_3$ (0.661 g, 4.99 mmol) and TMSCN (0.66 mL, 4.95 mmol) in 1,2-dichloroethane (17.0 mL) were reacted to give the desired product (0.1073 g, 34.1%). EI-MS m/z 315 (M$^+$) Rt (1.65 min).

4-[cyano(di-2-thienyl)methyl]-1-[3-(phenyloxy)propyl]-1-azoniabicyclo[2.2.2]octane bromide Following the general procedure outlined in Example 7, 1-azabicyclo[2.2.2]oct-4-yl(di-2-thienyl)acetonitrile (0.1073 g, 0.3412 mmol) and 3-bromopropyl phenyl ether (0.070 mL, 0.444 mmol) in 2CH$_3$CN/3CHCl$_3$ (6.5 mL) were reacted to give the desired product (0.1296 g, 72.0%). EI-MS m/z 449 (M$^+$) Rt (2.17 min).

Abbreviations

DCE 1,2-Dichloroethane
DMF Dimethylformamide
DMSO Dimethylsulfoxide
EI-MS Electrospray ionization—mass spectrometry
HPLC High pressure liquid chromatography
LDA Lithium disiopropylamide
TEA Triethylamine
TFA Trifluoroacetic acid
THF Tetrahydrofuran

BIOLOGICAL EXAMPLES

The inhibitory effects of compounds at the M$_3$ mAChR of the present invention are determined by the following in vitro and in vivo functional assays:

Analysis of Inhibition of Receptor Activation by Calcium Mobilization

Stimulation of mAChRs expressed on CHO cells were analyzed by monitoring receptor-activated calcium mobilization as previously described (H. M. Sarau et al, 1999. *Mol. Pharmacol.* 56, 657-663). CHO cells stably expressing M$_3$ mAChRs were plated in 96 well black wall/clear bottom plates. After 18 to 24 hours, media was aspirated and replaced with 100 µl of load media (EMEM with Earl's salts, 0.1% RIA-grade BSA (Sigma, St. Louis Mo.), and 4 µM Fluo-3-acetoxymethyl ester fluorescent indicator dye (Fluo-3 AM, Molecular Probes, Eugene, Oreg.) and incubated 1 hr at 37° C. The dye-containing media was then aspirated, replaced with fresh media (without Fluo-3 AM), and cells were incubated for 10 minutes at 37° C. Cells were then washed 3 times and incubated for 10 minutes at 37° C. in 100 µl of assay buffer (0.1% gelatin (Sigma), 120 mM NaCl, 4.6 mM KCl, 1 mM KH$_2$PO$_4$, 25 mM NaH CO$_3$, 1.0 mM CaCl$_2$, 1.1 mM MgCl$_2$, 11 mM glucose, 20 mM HEPES (pH 7.4)). 50 µl of compound (1×10$^{-11}$–1×10$^{-5}$ M final in the assay) was added and the plates were incubated for 10 min. at 37° C. Plates were then placed into a fluorescent light intensity plate reader (FLIPR, Molecular Probes) where the dye loaded cells were exposed to excitation light (488 nm) from a 6 watt argon laser. Cells were activated by adding 50 μl of acetylcholine (0.1-10 nM final), prepared in buffer containing 0.1% BSA, at a rate of 50 μl/sec. Calcium mobilization, monitored as change in cytosolic calcium concentration, was measured as change in 566 nm emission intensity. The change in emission intensity is directly related to cytosolic calcium levels. The emitted fluorescence from all 96 wells is measured simultaneously using a cooled CCD camera. Data points are collected every second. This data was then plotting and analyzed using GraphPad PRISM software.

Methacholine-Induced Bronchoconstriction—Potency and Duration of Action

Airway responsiveness to methacholine was determined in awake, unrestrained Balb C mice (n=6 each group). Barometric plethysmography was used to measure enhanced pause (Penh), a unitless measure that has been shown to correlate with the changes in airway resistance that occur during bronchial challenge with methacholine(2). Mice were pre-treated with 50 μl of compound (0.003-10 μg/mouse) in 50 μl of vehicle (10% DMSO) intranasally (i.n.) and were then placed in the plethysmography chamber a given amount of time following drug administration (15 min-96 h). For potency determination, a dose response to a given drug was performed, and all measurements were taken 15 min following i.n. drug administration. For duration of action determination, measurements were taken anywhere from 15 min to 96 hours following i.n. drug administration.

Once in the chamber, the mice were allowed to equilibrate for 10 min before taking a baseline Penh measurement for 5 minutes. Mice were then challenged with an aerosol of methacholine (10 mg/ml) for 2 minutes. Penh was recorded continuously for 7 min starting at the inception of the methacholine aerosol, and continuing for 5 minutes afterward. Data for each mouse were analyzed and plotted by using GraphPad PRISM software. This experiment allows the determination of duration of activity of the administered compound.

The present compounds are useful for treating a variety of indications, including but not limited to respiratory-tract disorders such as chronic obstructive lung disease, chronic bronchitis, asthma, chronic respiratory obstruction, pulmonary fibrosis, pulmonary emphysema, and allergic rhinitis.

Formulations-Administration

Accordingly, the present invention further provides a pharmaceutical formulation comprising a compound of formula (I), or a pharmaceutically acceptable salt, solvate, or physiologically functional derivative (e.g., salts and esters) thereof, and a pharmaceutically acceptable carrier or excipient, and optionally one or more other therapeutic ingredients.

Hereinafter, the term "active ingredient" means a compound of formula (I), or a pharmaceutically acceptable salt, solvate, or physiologically functional derivative thereof.

Compounds of formula (I) will be administered via inhalation via the mouth or nose.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di- or poly-saccharides (e.g., lactose or starch), organic or inorganic salts (e.g., calcium chloride, calcium phosphate or sodium chloride), polyalcohols (e.g., mannitol), or mixtures thereof, alternatively with one or more additional materials, such additives included in the blend formulation to improve chemical and/or physical stability or performance of the formulation, as discussed below, or mixtures thereof. Use of lactose is preferred. Each capsule or cartridge may generally contain between 20 μg-10 mg of the compound of formula (I) optionally in combination with another therapeutically active ingredient. Alternatively, the compound of the invention may be presented without excipients, or may be formed into particles comprising the compound, optionally other therapeutically active materials, and excipient materials, such as by co-precipitation or coating.

Suitably, the medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant as an inhaler having a reservoir form pack suitable for comprising multiple (un-metered doses) of medicament in dry powder form and including means for metering medicament dose from the reservoir to a delivery position. The metering means may for example comprise a metering cup or perforated plate, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

The formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament therefrom.

In one aspect, the multi-dose blister pack comprises plural blisters arranged in generally circular fashion on a disk-form blister pack. In another aspect, the multi-dose blister pack is elongate in form, for example comprising a strip or a tape.

Preferably, the multi-dose blister pack is defined between two members peelably secured to one another. U.S. Pat. Nos. 5,860,419, 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum aerodynamic particle size for inhalation into the bronchial system for localized delivery to the lung is usually 1-10 μm, preferably 2-5 μm. The optimum aerodynamic particle size for inhalation into the alveolar region for achieving systemic delivery to the lung is approximately 0.5-3 μm, preferably 1-3 μm. Particles having an aerodynamic size above 20 μm are generally too large when inhaled to reach the small airways. Average aerodynamic particle size of a formulation may measured by, for example cascade impaction. Average geometric particle size may be measured, for example by laser diffraction, optical means.

To achieve a desired particle size, the particles of the active ingredient as produced may be size reduced by conventional means eg by controlled crystallization, micronisation or nanomilling. The desired fraction may be separated out by air classification. Alternatively, particles of the desired size may be directly produced, for example by spray drying, controlling the spray drying parameters to generate particles of the desired size range. Preferably, the particles will be crystalline, although amorphous material may also be employed where desirable. When an excipient such as lactose is employed, generally, the particle size of the excipient will be much greater than the inhaled medicament within the present invention, such that the "coarse" carrier is non-respirable. When the excipient is lactose it will typically be present as milled lactose, wherein not more than 85% of lactose particles will have a MMD of 60-90 μm and not less than 15% will have a MMD of less than 15 μm. Additive materials in a dry powder blend in addition to the carrier may be either respirable, i.e., aerodynamically less than 10 microns, or non-respirable, i.e., aerodynamically greater than 10 microns.

Suitable additive materials which may be employed include amino acids, such as leucine; water soluble or water insoluble, natural or synthetic surfactants, such as lecithin (e.g., soya lecithin) and solid state fatty acids (e.g., lauric, palmitic, and stearic acids) and derivatives thereof (such as salts and esters); phosphatidylcholines; sugar esters. Additive materials may also include colorants, taste masking agents (e.g., saccharine), anti-static-agents, lubricants (see, for example, Published PCT Patent Appl. No. WO 87/905213, the teachings of which are incorporated by reference herein), chemical stabilizers, buffers, preservatives, absorption enhancers, and other materials known to those of ordinary skill.

Sustained release coating materials (e.g., stearic acid or polymers, e.g. polyvinyl pyrolidone, polylactic acid) may also be employed on active material or active material containing particles (see, for example, patent Nos. U.S. Pat. No. 3,634,582, GB 1,230,087, GB 1,381,872, the teachings of which are incorporated by reference herein).

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Preferred unit dosage formulations are those containing an effective dose, as herein before recited, or an appropriate fraction thereof, of the active ingredient.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of formula (I) as indicated below

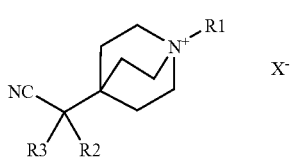

wherein:
R1 is selected from hydrogen, C1-15 alkyl, halosubstituted C1-15 alkyl, aryl C1-15 alkyl, C1-15 alkyl cycloalkyl, cycloalkyl, C2-15 alkenyl, hydroxy substituted C1-15 alkyl, C1-15 alkyl aryl, (CR7R7)qORa, (CR7R7)qNRaRa, (CR7R7)qNC(O)Ra, (CR7R7)qC(O)NRaRa, (CR7R7)qC(O)Ra, (CR7R7)qC(O)ORa, or (CR7R7)qOC(O)Ra; or R1 is:

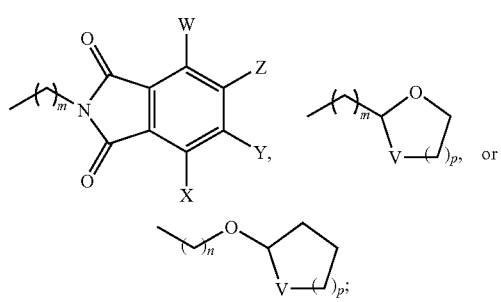

R2 and R3 are independently selected, from the group consisting of aryl, aryl C1-4 alkyl, C1-4 alkyl aryl, heteroaryl, heteroaryl C1-4 alkyl, C1-4 alkyl heteroaryl, heterocyclic, C1-4 alkyl heterocyclic and a heterocyclic C1-4 alkyl moiety;

Ra is selected from the group consisting of hydrogen, C1-15 alkyl, C1-15 alkoxy, aryl, aryl C1-15 alkyl, heteroaryl, heteroaryl C1-15 alkyl, heterocyclic and a heterocyclic C1-15 alkyl;

q is 0 or an integer having a value of 1 to 15;
n is an integer having a value of 1 to 14;
m is an integer having a value of 1 to 15;
p is an integer having a value of 1 to 4;
X, Y, Z and W are, independently, selected from the group consisting of hydrogen, C1-4 alkyl, C1-4 alkyl aryl, halosubstituted C1-4 alkyl, and hydroxy substituted C1-4 alkyl;

V is selected from the group consisting of O, S, and NRb;
Rb is selected from the group consisting of hydrogen, C1-4 alkyl and aryl C1-4 alkyl;

R7 is selected from the group consisting of hydrogen, C1-4 alkyl, halosubstituted C1-4 alkyl, and hydroxy substituted C1-4 alkyl; and X— is a physiologically acceptable anion.

2. A compound according to formula (II) herein below:

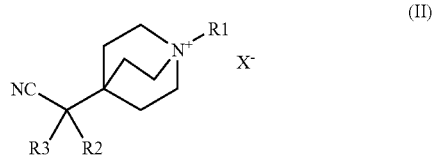

wherein:
R1 is selected from the group consisting of hydrogen, C1-10 alkyl, halosubstituted C1-10 alkyl, C1-10 alkyl aryl, C1-10 alkyl cycloalkyl, cycloalkyl, hydroxy substituted C1-10 alkyl, C2-5 alkenyl, and (CR7R7)qORa;

R2 and R3 are, independently, selected from the group consisting of:

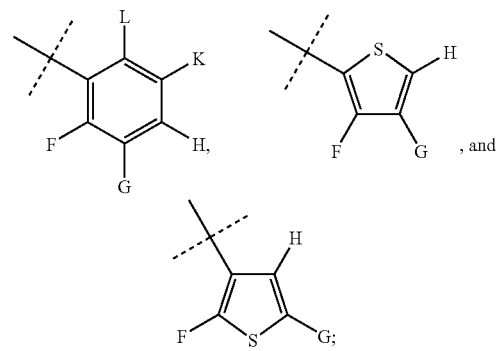

F, G, H, K and L are independently selected from the group consisting of hydrogen, halogen, cyano, C1-4 alkyl, halosubstituted C1-4 alkyl, hydoxy substituted C1-4 alkyl, and C1-4 alkoxy;

Ra is selected from the group consisting of hydrogen, C1-10 alkyl, C1-10 alkoxy, and C1-10 alkyl aryl; or Ra is:

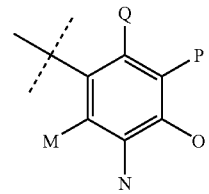

wherein:
M, N, O, P and Q are, independently, selected from the group consisting of hydrogen, halogen, cyano, nitro, and amino, C1-4 alkyl, halosubstituted C1-4 alkyl, hydroxy substituted C1-4 alkyl, and C1-4 alkoxy; or two of either M, N, O, P and Q moieties, together, form a 5 to 6 membered saturated or unsaturated ring;

q is 0 or an integer having a value of 1 to 10;
n is an integer having a value of 1 to 9;
m is an integer having a value of 1 to 10;
p is an integer having a value of 1 to 4;
V is selected from the group consisting of O, S, NH, and NHRb;

Rb is selected from the group consisting of hydrogen, C1-4 alkyl, and aryl C1-4 alkyl;

R7 is hydrogen or, C1-4 alkyl; and

X— is a physiologically acceptable anion, selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

3. A compound according to claim 1 selected from the group of:

4-[cyano(di-2-thienyl)methyl]-1-[3-(phenyloxy)propyl]-1-azoniabicyclo[2.2.2]octane bromide;

4-[cyano(diphenyl)methyl]-1-[3-(phenyloxy)propyl]-1-azoniabicyclo[2.2.2]octane bromide;

4-[cyano(diphenyl)methyl]-1-[2-(phenyloxy)ethyl]-1-azoniabicyclo[2.2.2]octane bromide;

4-[cyano(diphenyl)methyl]-1-[4-(phenyloxy)butyl]-1-azoniabicyclo[2.2.2]octane bromide;

4-[cyano(diphenyl)methyl]-1-{3-[(phenylmethyl)oxy]propyl}-1-azoniabicyclo[2.2.2]octane bromide;

4-[cyano(diphenyl)methyl]-1-nonyl-1-azoniabicyclo[2.2.2]octane bromide;

4-[cyano(diphenyl)methyl]-1-(2-phenylethyl)-1-azoniabicyclo[2.2.2]octane bromide;

4-[cyano(diphenyl)methyl]-1-[2-(methyloxy)ethyl]-1-azoniabicyclo[2.2.2]octane bromide;

4-[cyano(diphenyl)methyl]-1-ethyl-1-azoniabicyclo[2.2.2]octane bromide;

4-[cyano(diphenyl)methyl]-1-(2-{[2-(methyloxy)ethyl]oxy}ethyl)-1-azoniabicyclo[2.2.2]octane bromide;

4-[cyano(diphenyl)methyl]-1-(4-penten-1-yl)-1-azoniabicyclo[2.2.2]octane bromide;

1-azabicyclo[2.2.2]oct-4-yl(diphenyl)acetonitrile; and

4-[cyano(diphenyl)methyl]-1-(3-hydroxypropyl)-1-azoniabicyclo[2.2.2]octane bromide.

4. A pharmaceutical composition comprising a compound according to claim 1 and a pharmaceutically acceptable carrier thereof.

5. A method of inhibiting the binding of acetylcholine to a $M_3$ muscarinic acetylcholine receptor in the respiratory tract of a human in need thereof, which comprises contacting the $M_3$ muscarinic acetylcholine receptor with an effective amount of a compound according to claim 1 and wherein the method of contacting the receptor with the composition is via inhalation by the mouth or nose of the human.

6. The method according to claim 5 wherein the binding of the M3 muscarinic acetylcholine receptor is useful in the treatment of chronic obstructive lung disease, chronic bronchitis, asthma, chronic respiratory obstruction, pulmonary fibrosis, pulmonary emphysema or allergic rhinitis.

7. The method according to claim 5 wherein administration is via inhalation via the mouth.

8. The method according to claim 5 wherein administration is via a medicament dispenser selected from a reservoir dry powder inhaler, a multi-dose dry powder inhaler or a metered dose inhaler.

9. A method of synthesizing a compound according to claim 1, wherein R1 is hydrogen, comprising the step of:

pre-treating an alcohol according to formula III:

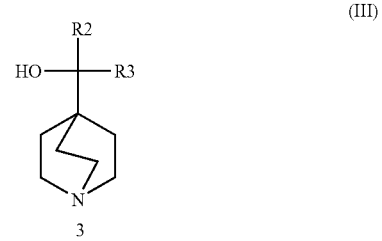

wherein;

R2 and R3 are, independently selected, from the group consisting of aryl, aryl C1-4 alkyl, C1-4 alkyl aryl, heteroaryl, heteroaryl C1-4 alkyl, C1-4 alkyl heteroaryl, heterocyclic, C1-4 alkyl heterocyclic and a heterocyclic C1-4 alkyl moiety;

with aluminum trichloride, $FeCl_3$, or $SnCl_4$, and TMSCN in an aprotic solvent.

10. The method according to claim 9 wherein the aprotic solvent is selected from the group consisting of dichloromethane, dichloroethane, toluene and benzene.

11. The method according to claim 10 wherein the solvent is dichloroethane and treatment is with aluminum trichloride.

12. The compound according to claim 1 wherein X— is selected from chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate.

13. The compound according to claim 1 wherein R1 and R2 are selected from phenyl or thiophene.

14. The compound according to claim 13 wherein R1 and R2 are both phenyl.

15. The compound according to claim 14 wherein R1 is hydrogen.

16. The compound according to claim 14 wherein R1 is C1-15 alkyl.

17. The compound according to claim 16 wherein R1 is nonane or ethyl.

18. The compound according to claim 14 wherein R1 is aryl C1-15 alkyl.

19. The compound according to claim 18 wherein R1 is phenethyl.

20. The compound according to claim 14 wherein R1 is C2-15 alkenyl.

21. The compound according to claim 20 wherein R1 is 4-penten-1-yl.

22. The compound according to claim 14 wherein R1 is a hydroxy substituted C1-15 alkyl.

23. The compound according to claim 22 wherein R1 is 3-hydroxypropyl.

24. The compound according to claim 14 wherein R1 is (CR7R7)qORa.

25. The compound according to claim 24 wherein Ra is C1-15 alkyl, aryl, or aryl C1-15 alkyl.

26. The compound according to claim 25 wherein R1 is 3-(phenyloxy)propyl, 2-(phenyloxy)ethyl, 4-(phenyloxy)butyl, 2-(methyloxy)ethyl, or 3-(phenylmethyloxy)propyl.

27. The compound according to claim 13 wherein R2 and R3 are both thienyl.

28. The compound according to claim 27 wherein R1 is (CR7R7)qORa.

29. The compound according to claim 28 wherein Ra is aryl.

30. The compound according to claim 29 wherein R1 is 3-(phenyloxy)propyl.

31. The compound according to claim 12 wherein X— is bromide.

32. The compound according to claim 2 wherein X— is bromide.

33. The compound which is 4-[cyano(diphenyl)methyl]-1-[2-(methyloxy)ethyl]-1-azoniabicyclo[2.2.2]octane bromide.

34. A pharmaceutical composition comprising a compound according to claim 33 and a pharmaceutically acceptable carrier thereof.

35. A method of synthesizing a compound of Formula (I) according to claim 1, comprising
a) treating an alcohol according to formula III:

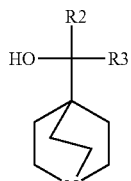

wherein;
R2 and R3 are, independently selected, from the group consisting of aryl, aryl C1-4 alkyl, C1-4 alkyl aryl, heteroaryl, heteroaryl C1-4 alkyl, C1-4 alkyl heteroaryl, heterocyclic, C1-4 alkyl heterocyclic and a heterocyclic C1-4 alkyl moiety;
with aluminum trichloride, $FeCl_3$, or $SnCl_4$ and TMSCN in an aprotic solvent; and
b) reacting the compound of step a) with R1X, in an organic solvent acetonitrile and chloroform to yield a compound of Formula (I), wherein R1 is as defined in claim 1 and X is a halide.

36. The method according to claim 35 wherein the aprotic solvent in step a) is selected from the group consisting of dichloromethane, dichloroethane, toluene and benzene.

37. The method according to claim 36 wherein the solvent is dichloroethane and treatment is with aluminum trichloride.

38. The method according to claim 35 wherein the organic solvent in step b) is chloroform or acetonitrile.

39. A method of treating chronic obstructive lung disease, chronic bronchitis, asthma, chronic respiratory obstruction, pulmonary fibrosis, pulmonary emphysema or allergic rhinitis in a human in need thereof, comprising administering to said human by inhalation via the mouth, an effective amount of a composition according to claim 1.

40. The method according to claim 39 wherein the treatment is for chronic obstructive lung disease or asthma.

41. A pharmaceutical composition comprising a compound according to claim 2 and a pharmaceutically acceptable carrier thereof.

42. The compound according to claim 2 wherein R1 is selected from the group consisting of C1-10 alkyl, C1-10 alkyl aryl, C2-5 alkenyl, and (CR7R7)qORa.

* * * * *